US010183179B1

(12) United States Patent
Smith et al.

(10) Patent No.: US 10,183,179 B1
(45) Date of Patent: Jan. 22, 2019

(54) TRIGGERED TREATMENT SYSTEMS AND METHODS

(71) Applicants: Varian Medical Systems, Inc., Palo Alto, CA (US); Varian Medical Systems International AG., Cham (CH)

(72) Inventors: Christel Smith, Santa Barbara, CA (US); Corey Zankowski, San Jose, CA (US); Jan Hein Timmer, Los Altos, CA (US); Wolfgang Kaissl, Wil (CH); Deepak Khuntia, Los Altos, CA (US); Eric Abel, San Jose, CA (US); Josh Star-Lack, Palo Alto, CA (US); Camille Noel, St. Louis, MO (US)

(73) Assignees: Varian Medical Systems, Inc., Palo Alto, CA (US); Varian Medical Systems International AG., Cham (CH)

( * ) Notice: Subject to any disclaimer, the term of this patent is extended or adjusted under 35 U.S.C. 154(b) by 0 days.

(21) Appl. No.: 15/657,072

(22) Filed: Jul. 21, 2017

(51) Int. Cl.
*A61N 5/00* (2006.01)
*A61N 5/10* (2006.01)
*A61B 90/00* (2016.01)

(52) U.S. Cl.
CPC ......... *A61N 5/1069* (2013.01); *A61N 5/1077* (2013.01); *A61B 2090/0481* (2016.02); *A61N 2005/1094* (2013.01)

(58) Field of Classification Search
CPC ...... A61N 5/10; A61N 5/1048; A61N 5/1049; A61N 5/1069; A61N 5/107; A61N 5/1071; A61N 5/103; A61N 2005/1058; A61N 2005/1061; A61N 2005/1062; A61N 5/00

USPC .......................................................... 378/65
See application file for complete search history.

(56) References Cited

U.S. PATENT DOCUMENTS

| | | |
|---|---|---|
| 5,834,787 A | 11/1998 | Bunker |
| 6,580,084 B1 | 6/2003 | Hiramoto et al. |
| 6,888,832 B2 | 5/2005 | Richardson et al. |
| 6,920,202 B1 | 7/2005 | Dinsmore |
| 7,423,278 B2 | 9/2008 | Amaldi et al. |
| 7,554,275 B2 | 6/2009 | Amaldi |

(Continued)

FOREIGN PATENT DOCUMENTS

| | | |
|---|---|---|
| EP | 3043863 A1 | 7/2016 |
| JP | 2014161706 A | 9/2014 |
| JP | 2017098000 A | 6/2017 |

OTHER PUBLICATIONS

Wen C. His, Michael F. Moyers, Dmitri Nichporov, Vladimir Anferov, Mark Wolanski, Chris E. Allgower, Jonathan B. Farr, Anthony E. Mascia, Andreis N. Schreuder, "Energy spectrum control for modulated proton beams", Medical Physics, (2009) 36(6) 2297-2308, http://www.ncbi.nlm.nih.gov/pmc/articles/PMC2832068/.

(Continued)

*Primary Examiner* — Jurie Yun

(57) ABSTRACT

In various embodiments, a radiation therapy method can include loading a planning image of a target in a human. In addition, the position of the target can be monitored. A computation can be made of an occurrence of substantial alignment between the position of the target and the target of the planning image. Furthermore, after the computing, a beam of radiation is triggered to deliver a dosage to the target in a short period of time (e.g., less than a second).

20 Claims, 8 Drawing Sheets

(56) References Cited

U.S. PATENT DOCUMENTS

| | | | |
|---|---|---|---|
| 7,778,691 B2 | 8/2010 | Zhang et al. | |
| 8,071,966 B2 | 12/2011 | Kaiser et al. | |
| 8,121,253 B2 | 2/2012 | Nelms | |
| 8,253,121 B2 | 8/2012 | Gnutzmann et al. | |
| 8,405,056 B2 | 3/2013 | Amaldi et al. | |
| 8,406,844 B2 | 3/2013 | Ruchala et al. | |
| 8,618,521 B2 | 12/2013 | Loo et al. | |
| 8,636,636 B2 | 1/2014 | Shukla et al. | |
| 8,644,571 B1 | 2/2014 | Schulte et al. | |
| 8,699,664 B2 | 4/2014 | Otto et al. | |
| 8,798,343 B2 * | 8/2014 | Kabus | A61B 6/5235 378/65 |
| 8,901,519 B2 | 12/2014 | Schardt et al. | |
| 8,986,186 B2 | 3/2015 | Zhang et al. | |
| 9,018,603 B2 | 4/2015 | Loo et al. | |
| 9,033,859 B2 | 5/2015 | Fieres et al. | |
| 9,149,656 B2 | 10/2015 | Tanabe | |
| 9,636,525 B1 | 5/2017 | Sahadevan | |
| 2002/0057760 A1 | 5/2002 | Carroll et al. | |
| 2006/0274061 A1 | 12/2006 | Wang et al. | |
| 2008/0049897 A1 * | 2/2008 | Molloy | A61N 5/1042 378/65 |
| 2009/0283702 A1 | 11/2009 | Umezawa et al. | |
| 2010/0003770 A1 | 1/2010 | Shibata et al. | |
| 2011/0006214 A1 | 1/2011 | Boenig | |
| 2011/0168903 A1 | 7/2011 | Kyele et al. | |
| 2012/0134470 A1 | 5/2012 | Shibuya et al. | |
| 2012/0136194 A1 | 5/2012 | Zhang et al. | |
| 2014/0265823 A1 | 9/2014 | Boisseau et al. | |
| 2014/0270086 A1 | 9/2014 | Krasnykh | |
| 2015/0011817 A1 | 1/2015 | Feng | |
| 2015/0057484 A1 | 2/2015 | Amaldi | |
| 2015/0117616 A1 | 4/2015 | Ishii et al. | |
| 2015/0306423 A1 | 10/2015 | Bharat et al. | |
| 2016/0193482 A1 * | 7/2016 | Fahrig | A61N 5/1078 600/1 |
| 2016/0225477 A1 | 8/2016 | Banine et al. | |
| 2016/0287905 A1 | 10/2016 | Liger | |
| 2016/0310764 A1 | 10/2016 | Bharadwaj et al. | |
| 2017/0028220 A1 | 2/2017 | Schulte et al. | |
| 2017/0203125 A1 | 7/2017 | Amato et al. | |

OTHER PUBLICATIONS

V. Anferov, M. Ball, G.P. Berg, B. Broderick, J. Collins, G. East, D. Friesel, D. Jenner, W.P. Jones, J. Katuin, S. Klein, C. Nelson, N. Schreuder, Wm. Starks, J. Self, "The Indiana University Midwest Proton Radiation Institute", Proceedings of the 2001 Particle Accelerator Conference, (2001) p. 645-64 https://accelconf.web.cern.ch/accelconf/p01/PAPERS/FOAA004.PDF.

Th. Haberer, W. Becher, D. Schardt, G. Kraft "Magnetic scanning system for heavy ion therapy" Nuclear Instruments and Methods in Physics Research Section A: Accelerators, Spectrometers, Detectors and Associated Equipment, NIM, Elsevie, Jun. 10 1993, vol. 330, Issues 1-2, Jun. 10, 1993, pp. 296-305.

Amaldi, Tera Foundation, Novara, Italy A. Degiovanni, Cern, Geneva, Switzerland Linac 2014. Proton and Carbon Linacs for Hadron Therapy U. http://accelconf.web.cern.ch/AccelConf/LINAC2014/papers/friob02.pdf.

Montay-Gruel P, Petersson K, Jaccard M, Boivin G, Germond JF, Petit B, Doenlen R, Favaudon V, Bochud F, Bailat C, Bourhis J, Vozenin MC. Irradiation in a flash: Unique sparing of memory in mice after whole brain irradiation with dose rates above 100Gy/s. Radiother Oncol. May 22, 2017. pii: S0167-8140(17)30365-1. doi: 10.1016/j.radonc.2017.05.003. [Epub ahead of print] PubMed PMID: 28545957.

Favaudon V, Caplier L, Monceau V, Pouzoulet F, Sayarath M, Fouillade C, Poupon Mf, Brito I, Hupé P, Bourhis J, Hall J, Fontaine JJ, Vozenin MC. Ultrahigh dose-rate Flash irradiation increases the differential response between normal and tumor tissue in mice. Sci Transl Med. Jul. 16, 2014;6(245):2451a93. doi: 10.1126/scitranslmed.3008973. PubMed PMID: 25031268.

Loo BW, Schuler E, Lartey FM, Rafat M, King GJ, Trovati S, Koong AC, Maxim PG. Delivery of Ultra-Rapid Flash Radiation Therapy and Demonstration of Normal Tissue Sparing After Abdominal Irradiation of Mice. International Journal of Radiation Oncology Biology Physics. vol. 98 Issue: 2 pp. E16-E16 Supplement: S Meeting Abstract: P003 Published: Jun. 1, 2017.

M. Bopp, H. Fitze, P. Sigg, and L. Stingelin "Upgrade concepts of the PSI accelerator RF systems for a projected 3 mA operation", Citation: AIP Conference Proceedings 600, 300 (2001); doi: 10.1063/1.1435259.

K. Peach, et al. "Pamela—A Model for an FFAG Based Hadron Therapy Machine", Proceedings of PAC07, Albuquerque, New Mexico, USA.

S. Benedetti, A. Grudiev, and A. Latina Phys. Rev. Accel. Beams 20, 040101—Published Apr. 13, 2017.

Z. Li, et. al., Normal conducting cw transverse crab cavity for producing short pulses in spear3, Proceedings of IPAC2017, Copenhagen, Denmark.

Valery Dolgashev, Sami Tantawi, Yasuo Higashi, Bruno Spataro, "Geometric dependence of radio-frequency breakdown in normal conducting accelerating structures," Applied Physics Letters, vol. 97, Issue 17, pp. 171501-171501-3, Oct. 2010.

Lisa Laurent, Sami Tantawi, Valery Dolgashev, Chris Nantista, Yasuo Higashi, Markus Aicheler, Samuli Heikkinen, and Walter Wuensch, Experimental Study of RF Pulsed Heating Phys. Rev. ST Accel. Beams 14, 041001 (2011) [21 pages].

S. Tantawi, Z. Li, patent pending, Title: "Distributed Coupling and Multi-Frequency Microwave Accelerators", Filed: Jul. 9, 2014, U.S. Appl. No. 62/022,469.

S.Tantawi, M.Nasr, "Designs and High Power Tests of Distributed Coupling Linacs" IFIC, Jun. 13-16, 2017, Valencia, Spainhttps://indico.cern.ch/event/589548/contributions/2615455/attachments/1479738/2294080/Mamdouh_High_Gradient_2017.pdf.

Jensen, Aaron, Jeff Neilson, and Sami Tantawi. "X-band multi-beam klystron design and progress report." Vacuum Electronics Conference (IVEC), 2015 IEEE International. IEEE, 2015.

K.Halbach, "Design of permanent multipole magnets with oriented rare earth cobalt material", Nuclear Instruments and Methods, vol. 169, Issue 1, Feb. 1, 1980, pp. 1-10 [http://www.sciencedirect.com/science/article/pii/0029554X80900944].

J. K. Lim, P. Frigola, G. Travish, J. B. Rosenzweig, S. G. Anderson, W. J. Brown, J. S. Jacob, C. L. Robbins, and A. M. Tremaine, "Adjustable, short focal length permanent-magnet quadrupole based electron beam final focus system" Phys. Rev. ST Accel. Beams 8, 072401—Published Jul. 15, 2005.

Sayyed Bijan Jiaa, Mohammad Hadi Hadizadeha, Ali Asghar Mowlavi ,Mandy Ebrahimi Loushab "Evaluation of energy deposition and secondary particle production in proton therapy of brain using a slab head phantom" Elsevier, Reports of Practical Oncology & Radiotherapy,vol. 19, Issue 6, Nov.-Dec. 2014, pp. 376-384.

J.Perl, J Shin, J Schümann, B Faddegon and H Paganetti, "TOPAS—An innovative proton Monte Carlo platform for research and clinical applications," Med. Phys. 39:6818-6837, 2012, PMID: 23127075, PMID: 23127075.

Lisa Polster, Jan Schuemann, Ilaria Rinaldi, Lucas Burigo, Aimee Louise McNamara, Robert D Stewart, Andrea Attili, David J. Carlson, Alejandro Carabe-Femadez, Bruce Faddegon, Joseph Perl, and Harald Paganetti, "Extension of TOPAS for the simulation of proton radiation on molecular and cellular endpoints," Phys Med Biol. Jun. 10, 2015;60 (13):5053-5070, PMID: 26061583.

Vladimir A. Bashkirov a,n , Robert P. Johnson b , Hartmut F.-W. Sadrozinski b , Reinhard W. Schulte a "Development of proton computed tomography detectors for applications in hadron therapy", NIM Nuclear Instruments and Methods in Physics Research A ( under press a the time of writing proposal) http://www.sciencedirect.com/science/article/pii/S0168900215009274 (abstract).

Qiyong Fan, Akshay Nanduri, Samuel Mazin, Lei Zhu, "Emission guided radiation therapy for lung and prostate cancers: A feasibility study on a digital patient", Med. Phys. 39 (11), Nov. 2012, 0094-2405/2012/39(11)/7140/13, 13 pages.

(56) References Cited

OTHER PUBLICATIONS

Vincent Favuadon, Laura Caplier, Virginie Monceau, Frederic Pouzoulet, Mano Sayarath, Charles Fouillade, Marie-France Poupon, Isabel Brito, Philippe Hupe, Jean Bounhis, Janet Hall, Jean-Jacques Fontaine, Marie-Catherine Vozenin, vol. 6 Issue 245 245ra93, www.ScienceTranslationalMedicine.org, UltraHigh dose-rate FLASH irradiation increase4s the differential response between normal and tumor tissue in mice, 9 pages, Jul. 16, 2014.

Radiotherapy "flashes" to reduce side effects, An effect for each mode of administration, Images of tissue sections, Ultra-high dose-rate, Science Translational Medicine, Jul. 16, 2014, 3 pages.

To introduce the concept of pseudo beam's-eye-view (pBEV), to establish a framework for computer-assisted beam orientation selection in intensity-modulated radiation therapy(IMRT), and to evaluate the utility of the proposed techniquie, Dec. 1, 2001 vol. 51, Issue 5, 3 pages, Pseudo beam's-eye-view as applied to beam orientation selection in intensity-modulated radiation therapy.

U. Amaldi et al., "Cyclinacs: Fast-Cycling Accelerators for Hadrontherapy," Nuclear Inst. and Methods in Physics Research, Mar. 2009.

S. Verdú-Andrés et al., "CABOTO, a high-gradient linac for hadrontherapy," Journal of Radiation Research, 2013, 54, pp. i155-i161.

A. Degiovanni et al., "Design of a Fast-Cycling High-Gradient Rotating Linac for Protontherapy," Proceedings of IPAC2013, Shanghai, China, THPWA008, 2013, pp. 3642-3644.

S. Verdú-Andrés et al., "Feasibility Study of a High-Gradient Linac for Hadrontherapy," Proceedings of IPAC2011, San Sebastián, Spain, WEPS045, 2011, pp. 2589-2591.

H. Paganetti et al., "Proton Beam Radiotherapy—The State of the Art," New Technologies in Radiation Oncology (Medical Radiation Series), Springer Verlag, Heidelberg, ISBN 3-540-00321-5, Oct. 2005, 36 pages.

* cited by examiner

TRIGGERED TREATMENT SYSTEMS AND METHODS

BACKGROUND

The use of radiation therapy to treat cancer is well known. Typically, radiation therapy involves directing a beam of high energy proton, photon, ion, or electron radiation ("therapeutic radiation") into a target or target volume (e.g., a tumor or lesion) in a patient.

Before a patient is treated with radiation, a treatment plan specific to that patient is developed. The plan defines various aspects of the therapy using simulations and optimizations based on past experiences. In general, the purpose of the treatment plan is to deliver sufficient radiation to the target while minimizing exposure of surrounding normal, healthy tissue to the radiation.

The planner's goal is to find a solution that is optimal with respect to multiple clinical goals that may be contradictory in the sense that an improvement toward one goal may have a detrimental effect on reaching another goal. For example, a treatment plan that spares the liver from receiving a dose of radiation may result in the stomach receiving too much radiation. These types of tradeoffs lead to an iterative process in which the planner creates different plans to find the one plan that is best suited to achieving the desired outcome.

A recent radiobiology study has demonstrated the effectiveness of delivering an entire, relatively high therapeutic radiation dose to a target within a single, short period of time. This type of treatment is referred to generally herein as FLASH radiation therapy (FLASH RT). Evidence to date suggests that FLASH RT advantageously spares normal, healthy tissue from damage when that tissue is exposed to only a single irradiation for only a very short period of time. FLASH RT thus introduces important constraints that are not considered in or achieved with conventional radiation treatment planning.

Typically for radiation therapy treatment, a patient first receives a CT (computed tomography) scan used to simulate the patient's treatment. A simulated treatment plan defines beam orientations and corresponding particle fluences to generate a 3D (three-dimensional) dose distribution that best achieves the physician's prescription and/or intent. Once the treatment plan has been defined, treatment can commence. It is noted that treatment uncertainties result from differences in the patient appearance at each treatment fraction compared to the CT simulation from which the treatment plan was derived. In addition, organ motion related to gross patient movement, breathing, heart function, and variable organ filling further compounds the treatment uncertainty. Various techniques are currently employed to manage organ motion in order to minimize the difference between the planned and delivered dose to the patient, including: breath holding, treatment gating, or abdominal compression. Each of these techniques has associated benefits and drawbacks, but all are designed to manage motion when treatment delivery time is over several minutes and may last as long as 60 minutes.

For example, one of the disadvantages of breath holding is that many patients do not have lung function to hold their breath for more than a few seconds; therefore, precluding them from holding their breath for the duration of an entire treatment field. It is noted that one of the disadvantages associated with treatment gating is that it requires continuous monitoring of the patient during relatively lengthy treatments, and turning the treatment beam off whenever the target volume moves outside of a predetermined volume of interest. Furthermore, treatment gating may increase the treatment time considerably, because the treatment beam may be held off for large periods of the breathing cycle. Note that abdominal compression is often poorly tolerated by most patients, as it places patients in a great deal of discomfort and can limit critical functions associated with normal organ motion, such as breathing or bowel motion.

SUMMARY

Various embodiments in accordance with the present disclosure can address the disadvantages described above.

In various embodiments, the present disclosure provides a triggered treatment which is a new paradigm of Image Guided Radiation Therapy that nearly eliminates organ motion during radiation delivery. In various embodiments, by delivering the entire treatment from each beam in a flash lasting a short period of time (e.g., a fraction of a second), target and organ motion is relatively "frozen" in 3D (three-dimensional) space and treatment uncertainty caused by motion is minimized. A method in accordance with various embodiments involves monitoring motion of the target volume of a patient before treatment, and selecting the appropriate time to trigger the flash of treatment. For each beam orientation, a region of interest can be monitored in real-time fluoroscopic projections through the patient. A single or multiple simultaneous fluoroscopic images can localize the target in three dimensions as it moves within the patient. When the target position matches its location within a pre-treatment simulation (e.g., CT (computed tomography), MRI (magnetic resonance imaging), or any medical imaging), the triggered treatment can be delivered precisely to the target in a nearly instantaneous flash.

In various embodiments, the triggered treatment of the present disclosure can include monitoring patient motion in real-time using fluoroscopic imaging (or alternate methods), which allows the patient to breathe freely or to hold their breath if indicated. In addition, this preserves patient comfort, ultimately making the patient experience more positive. Furthermore, it is noted that treatment margins that account for motion uncertainty can be markedly reduced due to the ultra-short triggered treatment flash, meaning that substantially less healthy tissue is irradiated, which should result in less side-effects and late toxicities resulting from the treatment.

In various embodiments, the triggered treatment of the present disclosure can include monitoring the patient surface continuously and triggering a sequence of radiographic images to be acquired to confirm the position of the target before triggering the treatment.

In various embodiments, the triggered treatment of the present disclosure can include any method of continuously tracking patient motion and/or breathing combined with some form of visualizing internal anatomy, fiducial markers, or surrogates of internal anatomy.

In various embodiments, the triggered treatment of the present disclosure can be implemented with any particle or wave radiation delivered at FLASH dose rates (e.g., greater than 40 Gy (grays)/second), but is not limited to such.

In various embodiments, in accordance with the present disclosure, it is noted that fluoroscopy (e.g., ionizing radiation) dose can be used with standard dose rates to reconstruct dose for inter-fractional dose tracking.

In various embodiments, a radiation therapy method can include loading a planning image of a target in a human. In addition, a four-dimensional (4D) real-time video image can be generated of the target. A computation can be made of an occurrence of substantial alignment between the target of the 4D real-time video image and the target of the planning image. Furthermore, after the computing, a beam of radiation is triggered to deliver a dosage to the target in a short period of time (e.g., less than a second).

In various embodiments, a radiation therapy method can include loading a planning image of a target in a human. Moreover, a 4D real-time video image can be generated of the target. A mapping can be performed of the target in both the 4D real-time video image and the planning image. A computation can be made of an occurrence of substantial alignment between the target of the 4D real-time video image and the target of the planning image. Additionally, after the computing, a beam of radiation is triggered to deliver a fraction of a dosage to the target in a short period of time (e.g., less than a second).

In various embodiments, a radiation therapy method can include loading a planning image of a target in a human. A 4D real-time video image can be generated of the target. In addition, a computation can be made of an occurrence of substantial alignment between the target of the 4D real-time video image and the target of the planning image. After the computing, a beam of radiation is triggered to deliver a dosage to the target in a short period of time (e.g., less than a second). Moreover, after the triggering, quality assurance is performed utilizing imaging information associated with the 4D real-time video image.

In various embodiments, a radiation therapy method can include loading a planning image of a target in a human. In addition, the position of the target can be monitored. A computation can be made of an occurrence of substantial alignment between the position of the target and the target of the planning image. Furthermore, after the computing, a beam of radiation is triggered to deliver a dosage to the target in less than a second.

In various embodiments, a radiation therapy method can include loading a planning image of a target in a human. Moreover, the position of the target can be monitored. A mapping can be performed of the target in both the monitoring and the planning image. A computation can be made of an occurrence of substantial alignment between the position of the target and the target of the planning image. Additionally, after the computing, a beam of radiation is triggered to deliver a fraction of a dosage to the target in less than a second.

In various embodiments, a radiation therapy method can include loading a planning image of a target in a human. The position of the target can be monitored. In addition, a computation can be made of an occurrence of substantial alignment between the position of the target and the target of the planning image. After the computing, a beam of radiation is triggered to deliver a dosage to the target in less than a second. Moreover, after the triggering, quality assurance is performed utilizing information associated with the monitoring.

While various embodiments in accordance with the present disclosure have been specifically described within this Summary, it is noted that the claimed subject matter are not limited in any way by these various embodiments.

BRIEF DESCRIPTION OF THE DRAWINGS

Within the accompanying drawings, various embodiments in accordance with the present disclosure are illustrated by way of example and not by way of limitation. It is noted that like reference numerals denote similar elements throughout the drawings.

DETAILED DESCRIPTION

Figure 1:
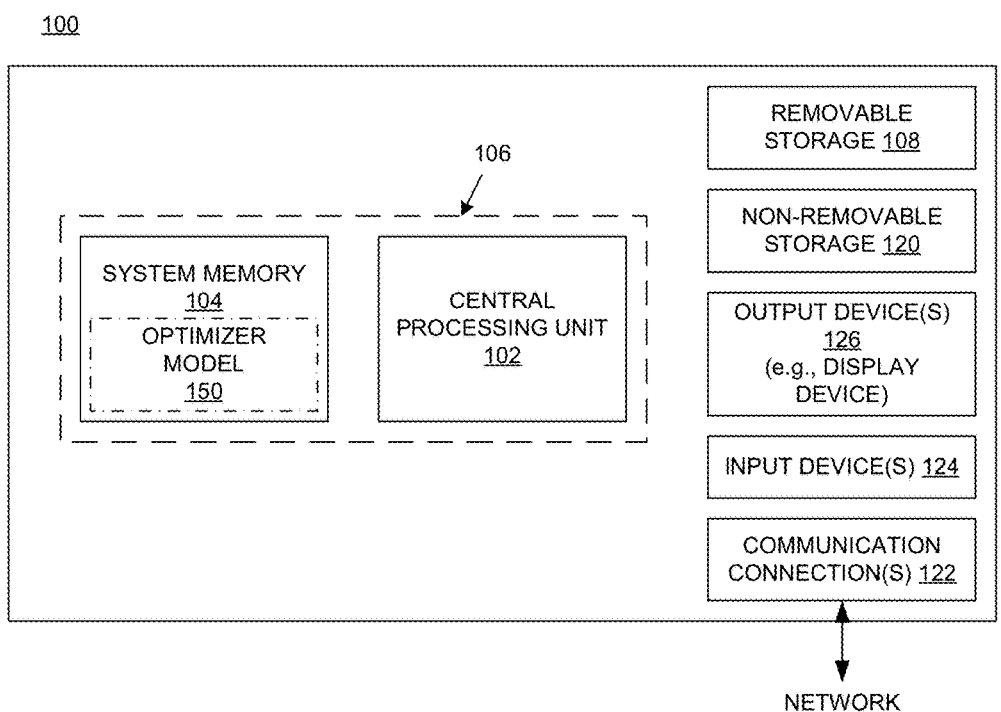
FIG. 1 is a block diagram of an example of a computing system upon which various embodiments described herein may be implemented in accordance with various embodiments of the present disclosure.

Reference will now be made in detail to various embodiments in accordance with the present disclosure, examples of which are illustrated in the accompanying drawings. While described in conjunction with various embodiments, it will be understood that these various embodiments are not intended to limit the present disclosure. On the contrary, the present disclosure is intended to cover alternatives, modifications and equivalents, which may be included within the scope of the present disclosure as construed according to the Claims. Furthermore, in the following detailed description of various embodiments in accordance with the present disclosure, numerous specific details are set forth in order to provide a thorough understanding of the present disclosure. However, it will be evident to one of ordinary skill in the art that the present disclosure may be practiced without these specific details or with equivalents thereof. In other instances, well known methods, procedures, components, and circuits have not been described in detail as not to unnecessarily obscure aspects of the present disclosure.

Some portions of the detailed descriptions that follow are presented in terms of procedures, logic blocks, processing, and other symbolic representations of operations on data bits within a computer memory. These descriptions and representations are the means used by those skilled in the data processing arts to most effectively convey the substance of their work to others skilled in the art. In the present application, a procedure, logic block, process, or the like, is conceived to be a self-consistent sequence of steps or instructions leading to a desired result. The steps are those utilizing physical manipulations of physical quantities. Usually, although not necessarily, these quantities take the form of electrical or magnetic signals capable of being stored, transferred, combined, compared, and otherwise manipulated in a computing system. It has proven convenient at times, principally for reasons of common usage, to refer to these signals as transactions, bits, values, elements, symbols, characters, samples, pixels, or the like.

It should be borne in mind, however, that all of these and similar terms are to be associated with the appropriate physical quantities and are merely convenient labels applied to these quantities. Unless specifically stated otherwise as apparent from the following discussions, it is appreciated that throughout the present disclosure, discussions utilizing terms such as "determining," "accessing," "directing," "controlling," "defining," "arranging," "generating," "acquiring," "triggering", "computing", "loading" or the like, refer to actions and processes of a computing system or similar electronic computing device or processor (e.g., the computing system 100 of FIG. 1). The computing system or similar electronic computing device manipulates and transforms data represented as physical (electronic) quantities within the computing system memories, registers or other such information storage, transmission or display devices. Terms such as "dose" or "fluence" generally refer to a dose or fluence value; the use of such terms will be clear from the context of the surrounding discussion.

Portions of the detailed description that follows are presented and discussed in terms of a method. Although steps and sequencing thereof are disclosed in figures herein describing the operations of this method, such steps and sequencing are exemplary. Any method is well suited to performing various other steps or variations of the steps recited in the flowchart of the figure herein, and in a sequence other than that depicted and described herein.

Various embodiments described herein may be discussed in the general context of computer-executable instructions residing on some form of computer-readable storage medium, such as program modules, executed by one or more computers or other devices. By way of example, and not limitation, computer-readable storage media may comprise non-transitory computer storage media and communication media. Generally, program modules include routines, programs, objects, components, data structures, etc., that perform particular tasks or implement particular abstract data types. The functionality of the program modules may be combined or distributed as desired in various embodiments.

Computer storage media includes volatile and nonvolatile, removable and non-removable media implemented in any method or technology for storage of information such as computer-readable instructions, data structures, program modules or other data. Computer storage media includes, but is not limited to, random access memory (RAM), read only memory (ROM), electrically erasable programmable ROM (EEPROM), flash memory or other memory technology, compact disk ROM (CD-ROM), digital versatile disks (DVDs) or other optical storage, magnetic cassettes, magnetic tape, magnetic disk storage or other magnetic storage devices, or any other medium that can be used to store the desired information and that can be accessed to retrieve that information.

Communication media can embody computer-executable instructions, data structures, and program modules, and includes any information delivery media. By way of example, and not limitation, communication media includes wired media such as a wired network or direct-wired connection, and wireless media such as acoustic, radio frequency (RF), infrared and other wireless media. Combinations of any of the above can also be included within the scope of computer-readable media.

FIG. 1 shows a block diagram of an example of a computing system 100 upon which various embodiments described herein may be implemented in accordance with various embodiments of the present disclosure. In its most basic configuration, the system 100 includes at least one processing unit 102 and memory 104. This most basic configuration is illustrated in FIG. 1 by dashed line 106. The system 100 may also have additional features and/or functionality. For example, the system 100 may also include additional storage (removable and/or non-removable) including, but not limited to, magnetic or optical disks or tape. Such additional storage is illustrated in FIG. 1 by removable storage 108 and non-removable storage 120. The system 100 may also contain communications connection(s) 122 that allow the device to communicate with other devices, e.g., in a networked environment using logical connections to one or more remote computers.

The system 100 also includes input device(s) 124 such as keyboard, mouse, pen, voice input device, touch input device, etc. Output device(s) 126 such as a display device, speakers, printer, etc., are also included.

In the example of FIG. 1, the memory 104 includes computer-readable instructions, data structures, program modules, and the like associated with an "optimizer" model 150. However, the optimizer model 150 may instead reside in any one of the computer storage media used by the system 100, or may be distributed over some combination of the computer storage media, or may be distributed over some combination of networked computers. The functionality of the optimizer model 150 is described below.

It is noted that the computing system 100 may not include all of the elements illustrated by FIG. 1. In addition, the computing system 100 can be implemented to include one or more elements not illustrated by FIG. 1. It is pointed out that the computing system 100 can be utilized or implemented in any manner similar to that described and/or shown by the present disclosure, but is not limited to such.

Figure 2:
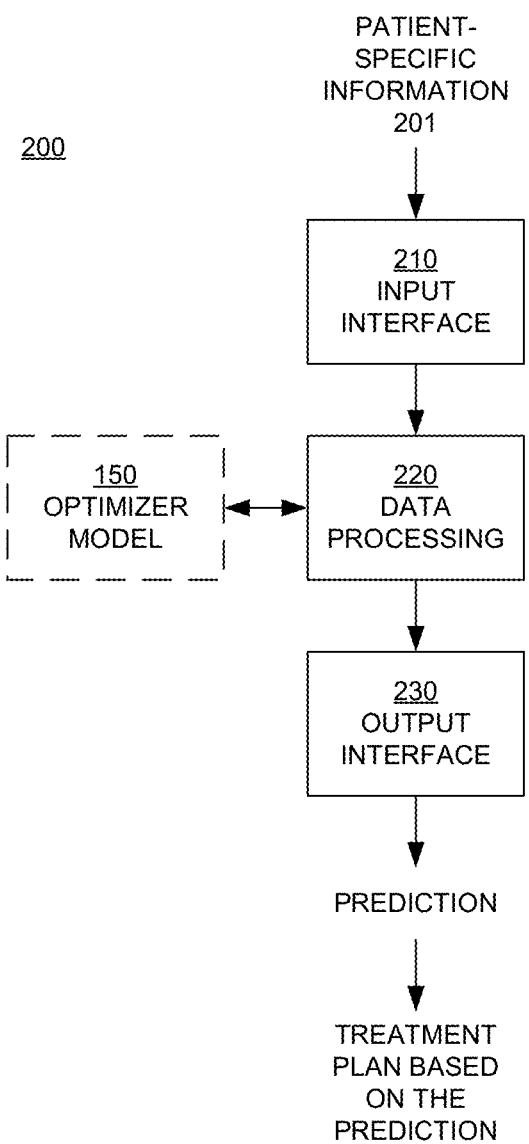
FIG. 2 is a block diagram illustrating an example of an automated radiation therapy treatment planning system in accordance with various embodiments of the present disclosure.

FIG. 2 is a block diagram illustrating an example of an automated radiation therapy treatment planning system 200 in accordance with various embodiments of the present disclosure. The system 200 includes an input interface 210 to receive patient-specific information (data) 201, a data processing component 220 that implements the optimizer model 150, and an output interface 230. The system 200 in whole or in part may be implemented as a software program, hardware logic, or a combination thereof on/using the computing system 100 (FIG. 1).

In the example of FIG. 2, the patient-specific information is provided to and processed by the optimizer model 150. The optimizer model 150 yields a prediction result. A treatment plan based on the prediction result can then be generated.

Note that the system 200 may not include all of the elements illustrated by FIG. 2. Furthermore, the system 200 can be implemented to include one or more elements not illustrated by FIG. 2. It is pointed out that the system 200 can be utilized or implemented in any manner similar to that described and/or shown by the present disclosure, but is not limited to such.

Figure 3:
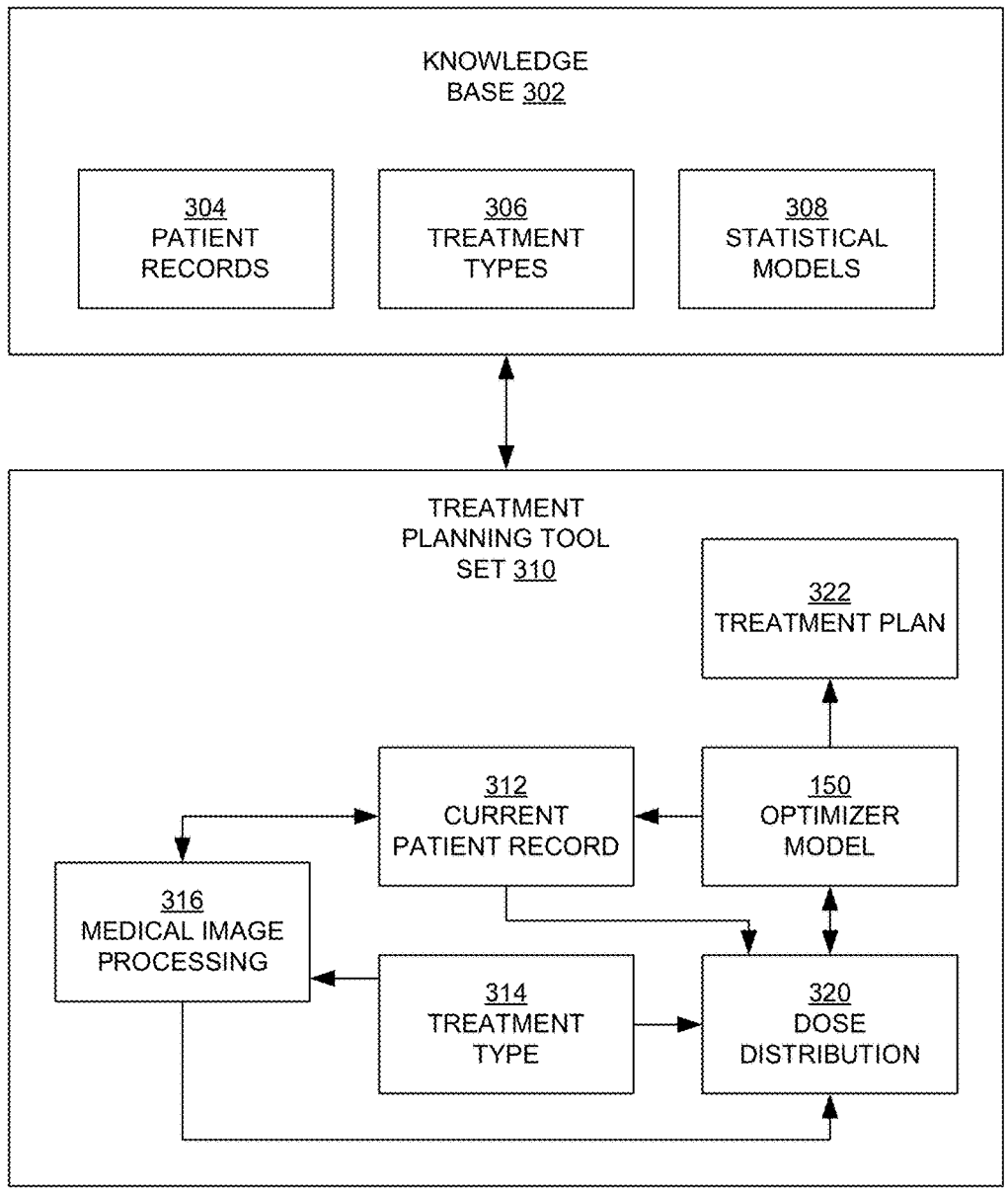
FIG. 3 illustrates a knowledge-based planning system in accordance with various embodiments of the present disclosure.

FIG. 3 illustrates a knowledge-based planning system 300 in accordance with various embodiments of the present disclosure. In the example of FIG. 3, the system 300 includes a knowledge base 302 and a treatment planning tool set 310. The knowledge base 302 includes patient records 304 (e.g., radiation treatment plans), treatment types 306, and statistical models 308. The treatment planning tool set 310 in the example of FIG. 3 includes a current patient record 312, a treatment type 314, a medical image processing module 316, the optimizer model (module) 150, a dose distribution module 320, and a final radiation treatment plan 322.

The treatment planning tool set 310 searches through the knowledge base 302 (through the patient records 304) for prior patient records that are similar to the current patient record 312. The statistical models 308 can be used to compare the predicted results for the current patient record 312 to a statistical patient. Using the current patient record 312, a selected treatment type 306, and selected statistical models 308, the tool set 310 generates a radiation treatment plan 322.

More specifically, in FIG. 3, based on past clinical experience, when a patient presents with a particular diagnosis, stage, age, weight, sex, co-morbidities, etc., there can be a treatment type that is used most often. By selecting the treatment type that the planner has used in the past for similar patients, a first-step treatment type 314 can be chosen. The medical image processing module 316 provides automatic contouring and automatic segmentation of two-dimensional cross-sectional slides (e.g., from computed tomography (CT), magnetic resonance imaging (MRI), or other medical imaging) to form a three-dimensional (3D) image using the medical images in the current patient record 312. Dose distribution maps are calculated by the dose distribution module 320, which may utilize the optimizer model 150.

In various embodiments according to the present disclosure, the optimizer model 150 uses a dose prediction model to help shape the dose distribution. The optimizer model 150 can provide, for example, a 3D dose distribution, fluences, and associated dose-volume histograms for the current patient.

It is pointed out that the system 300 may not include all of the elements illustrated by FIG. 3. Moreover, the system 300 can be implemented to include one or more elements not illustrated by FIG. 3. Note that the system 300 can be utilized or implemented in any manner similar to that described and/or shown by the present disclosure, but is not limited to such.

Figure 4A:
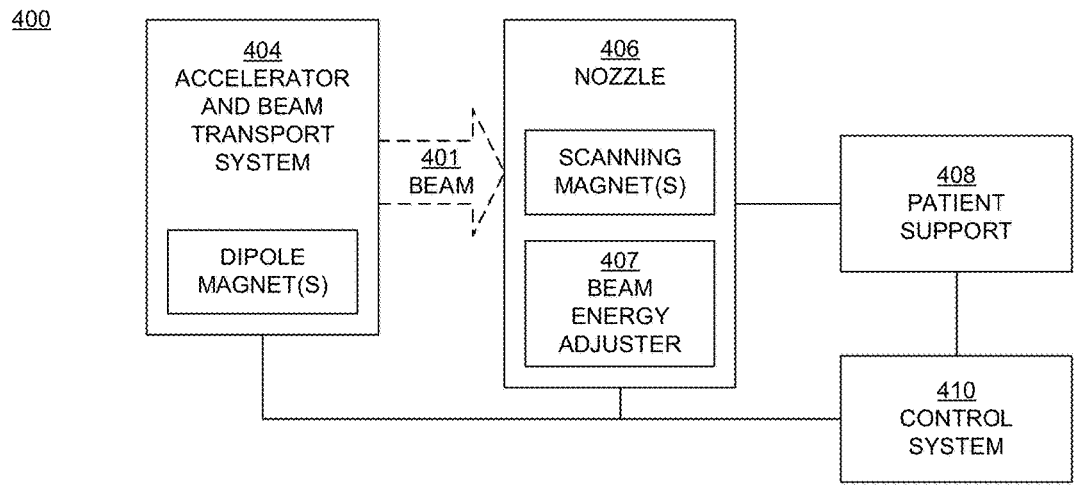
FIG. 4A is a block diagram showing selected components of a radiation therapy system upon which various embodiments can be implemented in accordance with various embodiments of the present disclosure.

FIG. 4A is a block diagram showing selected components of a radiation therapy system 400 upon which various embodiments can be implemented in accordance with various embodiments of the present disclosure. In the example of FIG. 4A, the system 400 includes an accelerator and beam transport system 404 and a nozzle 406.

The accelerator and beam transport system 404 generates and accelerates a beam of charged particles, such as electrons, protons, and ions (e.g., heavy ions), and contains the particles in a well-defined beam. In various embodiments, the accelerator is an isochronous cyclotron capable of continuous wave output. The accelerator (e.g., the cyclotron) extracts particles with a specified energy. This provides a high, continuous wave beam current for the high dose rate per shot. Other types of radio frequency accelerators can be used, such as a pulsed proton accelerator such as a synchrocyclotron, a synchrotron, a coupled cavity linear accelerator in addition to non-radio frequency accelerators, such as constant field, and laser-based accelerators. The accelerator (e.g., cyclotron) can be a lower power output cyclotron, such as a cyclotron that accelerates particles to the range of 70-300 million electron volts (MeVs).

Within FIG. 4A, the accelerator and beam transport system 404 includes components (e.g., dipole magnets, also known as bending magnets) that direct (e.g., bend, steer, or guide) the beam through the accelerator and beam transport system in a direction toward and into the nozzle 406. The accelerator and beam transport system 404 may also include one or more multileaf collimators (MLCs); each MLC leaf can be independently moved back-and-forth by the control system 410 to dynamically shape an aperture through which the beam can pass, to block or not block portions of the beam and thereby control beam shape and exposure time. The accelerator and beam transport system 404 may also include components that are used to adjust the beam energy entering the nozzle 406 so that it is different from the beam energy extracted from the accelerator. In various embodiments, sets of quadrupole magnets are located along the beam paths in the accelerator and beam transport system 404.

In various embodiments, it is noted that the accelerator and beam transport system 404 of the therapy system 400 can be implemented to produce any type of particle beam. For example, in various embodiments, the accelerator and beam transport system 404 can be implemented to produce any type of charged particle beam or non-charged particle beam. It is noted that in various embodiments the accelerator and beam transport system 404 can produce a particle beam of, but not limited to, electrons, protons, photons, carbon, carbon ions, neutrons, helium, alpha particles, oxygen, helium nuclei, or X-rays. In addition, in various embodiments, the accelerator and beam transport system 404 can be implemented to produce an ultra-sound output.

The nozzle 406 is used to aim the beam toward various locations (a target) within an object (e.g., a patient) supported on the patient support device 408 (e.g., a chair or table) in a treatment room. A target may be an organ, a portion of an organ (e.g., a volume or region within the organ), a tumor, diseased tissue, or a patient outline. In various embodiments, the nozzle 406 also includes components (e.g., X-Y scanning magnets) that steer (e.g., guide, deflect, or scan) the beam particles in the X and Y directions, to scan a target in a patient on the patient support device 408.

Within FIG. 4A, the nozzle 406 may be mounted on or a part of a gantry (e.g., FIGS. 4B, 4C, and 4D) that can be moved relative to the patient support device 408, which may also be moveable. In various embodiments, the accelerator and beam transport system 404 is also mounted on or is a part of the gantry; in various embodiments, the accelerator and beam transport system is separate from (but in communication with) the gantry.

The control system 410 of FIG. 4A receives and implements a prescribed treatment plan. In various embodiments, the control system 410 includes a computer system having a processor, memory, an input device (e.g., a keyboard), and perhaps a display in well-known fashion. The control system 410 can receive data regarding operation of the system 400. The control system 410 can control parameters of the accelerator and beam transport system 404, nozzle 406, and patient support device 408, including parameters such as the energy, intensity, direction, size, and/or shape of the beam, according to data it receives and according to the prescribed treatment plan.

As noted above, the particles entering the nozzle 406 have a specified energy. Thus, in various embodiments according to the present disclosure, the nozzle 406 includes one or more components that affect (e.g., decrease, modulate) the energy, intensity, or both energy and intensity of the particles in the beam. The term "beam modulator" is used herein as a general term for a component or components that affect the energy, intensity, or both energy and intensity of the particles in the beam, in order to control the range of the beam (e.g., the extent that the beam penetrates into a target) and/or to control the depth dose curve of the beam (e.g., the location of the maximal dose value in the target). In various embodiments, the beam modulator 407 includes a range modulator, a range shifter, an intensity modulator, or any combination thereof (e.g., a range modulator and a range shifter, a range and intensity modulator, etc.). That is, when the term "beam modulator" is used, then the element being discussed may be a range modulator, an intensity modulator, a range shifter, or both a range modulator and a range shifter, or a range and intensity modulator, or intensity modulator, or intensity modulator and range shifter. Examples of beam modulators are disclosed in the co-pending patent application, U.S. application Ser. No. 15/089,330, entitled "Radiation Therapy Systems and Methods" (as-filed); however, the present disclosure is not so limited.

Note that the system 400 may not include all of the elements illustrated by FIG. 4A. In addition, the system 400 can be implemented to include one or more elements not illustrated by FIG. 4A. It is pointed out that the system 400 can be utilized or implemented in any manner similar to that described and/or shown by the present disclosure, but is not limited to such.

Figure 4B:
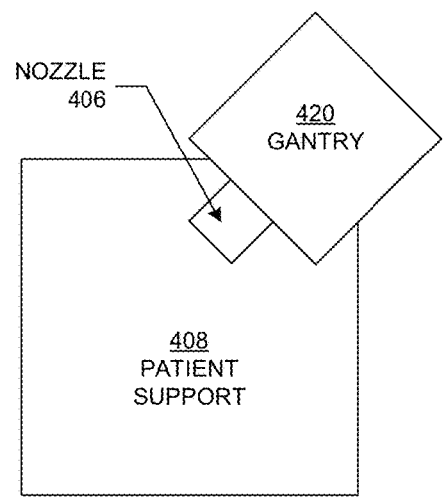
FIG. 4B is a block diagram illustrating a non-coplanar arrangement of a gantry and nozzle relative to a patient support device in accordance with various embodiments of the present disclosure.
Figure 4C:
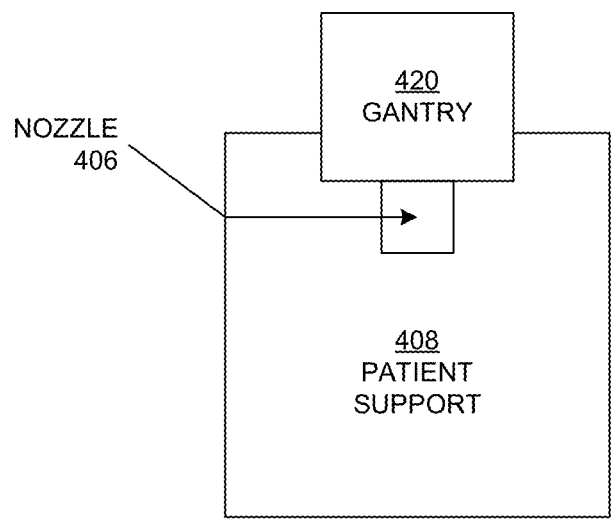
FIG. 4C is a block diagram illustrating a coplanar arrangement of a gantry and nozzle relative to a patient support device in accordance with various embodiments of the present disclosure.
Figure 4D:
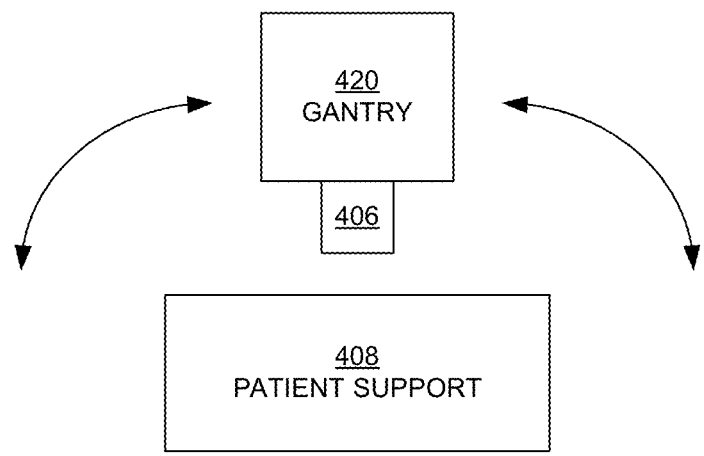
FIG. 4D is a block diagram illustrating movement of a gantry and nozzle around a patient support device in accordance with various embodiments of the present disclosure.

FIG. 4B is a block diagram illustrating a non-coplanar arrangement of a gantry 420 and nozzle 406 relative to a patient support device 408 in accordance with various embodiments of the present disclosure. FIG. 4C is a block diagram illustrating a coplanar arrangement of a gantry 420 and nozzle 406 relative to a patient support device 408 in accordance with various embodiments of the present disclosure. FIG. 4D is a block diagram illustrating movement of the gantry 420 and nozzle 406 around the patient support device 408 in accordance with various embodiments of the present disclosure. This movement can occur in either the non-coplanar arrangement or the coplanar arrangement.

Figure 5:
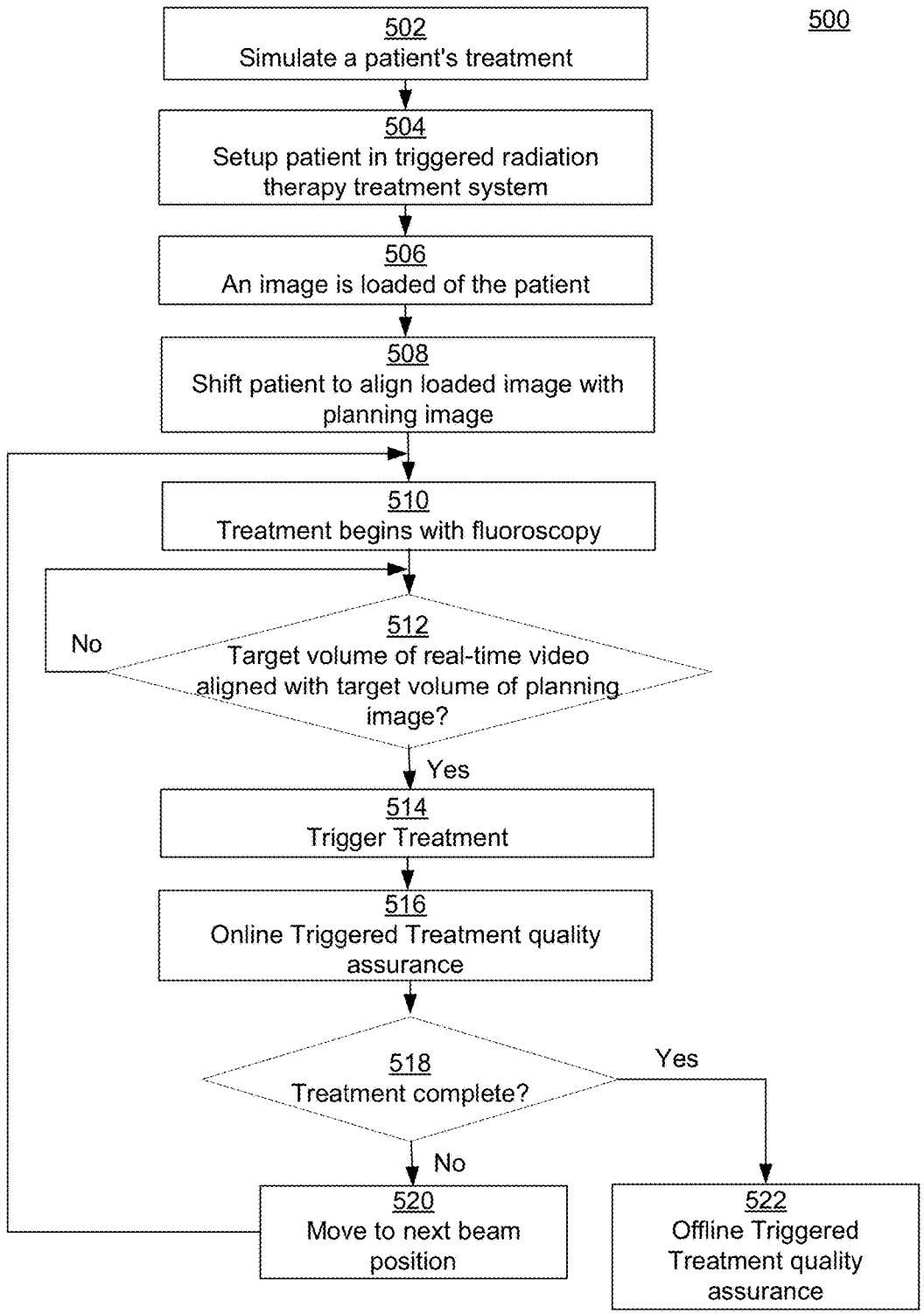
FIG. 5 is a flow diagram of a method in accordance with various embodiments of the present disclosure.

FIG. 5 is a flow diagram of a method 500 for performing triggered radiation therapy treatment in accordance with various embodiments of the present disclosure. Although specific operations are disclosed in FIG. 5, such operations are examples. The method 500 may not include all of the operations illustrated by FIG. 5. Also, method 500 may include various other operations and/or variations of the operations shown. Likewise, the sequence of the operations of flow diagram 500 can be modified. It is appreciated that not all of the operations in flow diagram 500 may be performed. In various embodiments, one or more of the operations of method 500 can be controlled or managed by software, by firmware, by hardware or by any combination thereof, but is not limited to such. Method 500 can include processes of various embodiments of the present disclosure which can be controlled or managed by a processor(s) and electrical components under the control of computer or computing device readable and executable instructions or code (e.g., the optimizer model 150 of FIG. 1). The computer or computing device readable and executable instructions (or code) may reside, for example, in data storage features such as computer or computing device usable volatile memory, computer or computing device usable non-volatile memory, and/or computer or computing device usable mass data storage. However, the computer or computing device readable and executable instructions (or code) may reside in any type of computer or computing device readable medium or memory (e.g., like those found within the computing system 100 of FIG. 1).

At operation 502, simulate a patient's treatment. Note that operation 502 can be implemented in a wide variety of ways. For example, in various embodiments, operation 502 can include the patient receiving a scan (e.g., CT (computed tomography), MRI (magnetic resonance imaging), or other medical imaging) of one or more target volumes used to simulate the patient's treatment. In various embodiments, the scan(s) at operation 502 can be referred to as a planning image(s) and can be loaded into one or more computing system memory devices. It is noted that operation 502 can be implemented in any manner similar to that described and/or shown by the present disclosure, but is not limited to such.

At operation 504 of FIG. 5, a patient is setup within a triggered radiation therapy treatment system. It is noted that operation 504 can be implemented in a wide variety of ways. For example, in various embodiments, the patient setup at operation 504 may employ less rigid patient positioning techniques such as the patient laying on a couch or being seated in a chair that are frameless and/or maskless. Note that operation 504 can be implemented in any manner similar to that described and/or shown by the present disclosure, but is not limited to such.

At operation 506, an image (e.g., static or non-static) is loaded of at least one target volume of the patient. Note that operation 506 can be implemented in a wide variety of ways. For example, the image can be loaded at operation 506 by utilizing a cone beam computed tomography (CBCT) scan, an MRI scan, or any other medical imaging scan of the patient, but is not limited to such. Operation 506 can be implemented in any manner similar to that described and/or shown by the present disclosure, but is not limited to such.

At operation 508 of FIG. 5, based on the loaded image, the patient may be shifted or moved in order to align the patient to the ideal target orientation of a planning image used to simulate the patient's treatment. It is noted that operation 508 can be implemented in a wide variety of ways. For example, using the loaded image, the couch or chair that the patient is on or in can be 3D shifted at operation 508 in order to align the patient with the planning image (e.g., CT, MRI, or other medical imaging) used to simulate the patient's treatment, but is not limited to such. Note that operation 508 can be implemented in any manner similar to that described and/or shown by the present disclosure, but is not limited to such.

At operation 510, treatment of the patient begins with real-time fluoroscopic imaging. Note that operation 510 can be implemented in a wide variety of ways. For example, a four dimensional (4D) cone beam can be generated at operation 510 thereby resulting in a real-time video feed. It is noted that operation 510 can be implemented in any manner similar to that described and/or shown by the present disclosure, but is not limited to such.

At operation 512 of FIG. 5, a computation can be made (e.g., manually or automatically) as to whether the target volume of the real-time video imaging substantially aligns with the target volume of the planning image. If so, method 500 can proceed to operation 514. However, if at operation 512 it is computed that the target volume of the real-time video imaging does not substantially align with the target volume of the planning image, method 500 can proceed to the beginning of operation 512.

It is noted that operation 512 can be implemented in a wide variety of ways. For example, at operation 512, a manual monitoring can be implemented by a human (e.g., a therapist) that is trained to watch the real-time video imaging of the patient and determine when the target volume substantially aligns (e.g., within a range of deviation) with the intended target volume from the planning image (e.g., CT, MRI, or other medical imaging). In various embodiments, at operation 512, an automatic monitoring can be included using a computing system (e.g., 100) wherein one or more metrics are defined in order to compute when the target volume substantially aligns (e.g., within a range of deviation) with the intended target volume from the planning image (e.g., CT, MRI, or other medical imaging).

Figure 6:
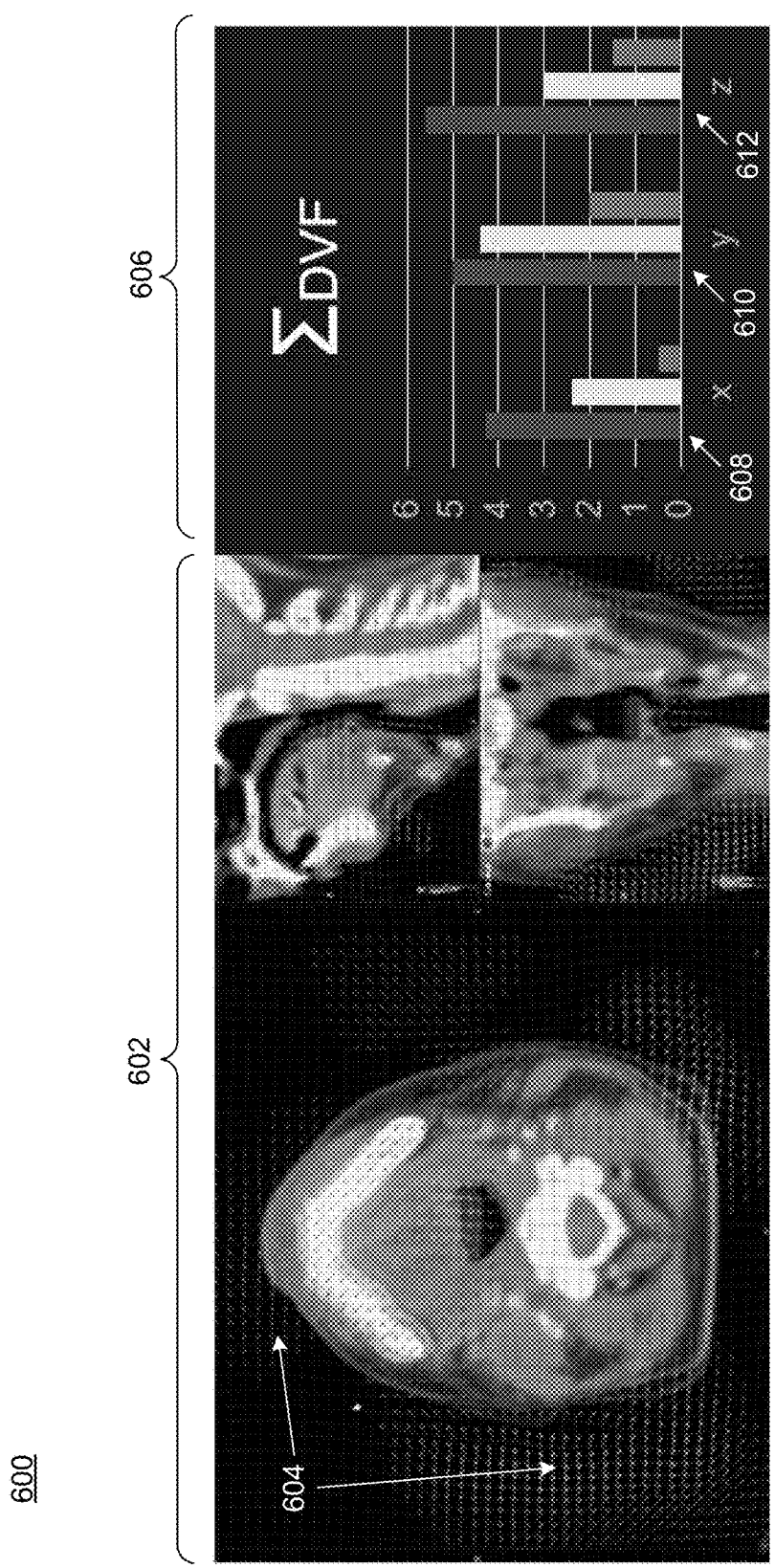
FIG. 6 illustrates a visual representation in accordance with various embodiments of the present disclosure.

In various embodiments, operation 512 of FIG. 5 can be implemented utilizing a visual representation of the mapping and alignment (e.g., within a range of deviation) of the real-time video imaging and the target volume of the planning image (e.g., CT, MRI, or other medical imaging). For example, FIG. 6 illustrates a visual representation 600 of the sum of a real-time deformation vector-field with colors in accordance with various embodiments of the present disclosure. More specifically, the visual representation 600 illustrates the sum of a real-time deformation vector-field with colors guiding a human user (e.g., therapist) to when the vector field magnitude is minimizing. Note that when the vector field magnitude is minimizing, the real-time video imaging of the target volume substantially aligns (e.g., within a range of deviation) with the target volume of the planning image.

It is noted that the visual representation 600 in various embodiments can include a deformation vector-field images 602 and a bar graph 606. The visual representation 600 can be generated by doing a deformable image registration where each voxel of the real-time video imaging will be mapped to a voxel in the planning image and that voxel mapping can be represented by deformation vector-fields 604 as shown in the vector-field images 602. It is pointed out that where there is a lot of change from one image to the other is represented by long arrows or vectors 604 and where there is not so much is represented by small arrows 604. Therefore, when the lengths of the arrows 604 get minimized within a region of interest (e.g., target volume), the treatment beam can be triggered (e.g., at operation 514). In addition, in various embodiments, the arrows 604 can be color coded where lighter colors indicate areas of higher deformation between the images while darker colors indicate areas of less deformation, but is not limited to such.

Within FIG. 6, in various embodiments, the bar graph 606 illustrates the summing of the deformation vector-field in each direction resulting in a quick activation of the magnitude of how long those arrows are in the x, y, and z directions. Within the bar graph 606, each of the x, y and z would include a bar 608, 610, or 612, respectively, indicating how close the first image is to being aligned with the second image (e.g., planning image). The shorter the bar, the closer the two images are aligned. Conversely, the longer the bar, the larger the two images are misaligned. In various embodiments, the bars can each be color coded. For example, a red bar represents misalignment between the two images, a yellow bar represents better alignment, and a green bar indicates an acceptable or desirable range of alignment between the two images. In various embodiments of the bar graph 606, it is noted that each of the x, y and z would include a single bar 608, 610, or 612, respectively, that can change in real-time.

Note that the visual representation 600 may not include all of the elements illustrated by FIG. 6. In addition, the visual representation 600 can be implemented to include one or more elements not illustrated by FIG. 6. It is pointed out that the visual representation 600 can be utilized or implemented in any manner similar to that described and/or shown by the present disclosure, but is not limited to such.

Within FIG. 5, operation 512 can be implemented utilizing a different visual representation than that shown within FIG. 6. For example, in various embodiments, a visual representation can enable the "drawing" of a three-dimensional volume around a target area or region of interest. Within that region of interest, the magnitude of the real-time deformation vector-field can be summed in real-time resulting in a metric (e.g., a number that is changing in real-time). When that number gets minimized (or within a defined range), a treatment beam can be triggered (e.g., at operation 514). Note that operation 512 can be implemented in any manner similar to that described and/or shown by the present disclosure, but is not limited to such.

At operation 514, a treatment is triggered which can include, but is not limited to, delivering a dose of radiation therapy (or ultrasound, etc.) to the target volume within a fraction of a second (e.g., less than a second). Note that operation 514 can be implemented in a wide variety of ways. For example, at operation 514, the entire treatment dosage of radiation therapy can be delivered to the target volume within a fraction of a second. In various embodiments, at operation 514, a fraction of the treatment dosage of radiation therapy can be delivered to the target volume within a fraction of a second. In various embodiments, at operation 514, each beam can deliver a relatively high dose in a relatively short period of time. For example, each beam can deliver, but is not limited to, at least 0.01 grays (Gy) or 4 Gy in less than one second, and may deliver as much as 20 Gy or 500 Gy or more in less than one second (sec). In various embodiments, at operation 514, each beam can deliver, but is not limited to, greater than 4 Gy/sec, greater than 20 Gy/sec, or greater than 40 Gy/sec. In various embodiments, at operation 514, each beam can deliver, but is not limited to, at least 1 Gy in 0.25 sec, at least 1 Gy in 0.05 sec, or at least 1 Gy in 0.025 sec. It is noted that operation 514 can be implemented in any manner similar to that described and/or shown by the present disclosure, but is not limited to such.

At operation 516 of FIG. 5, an online (or during treatment) triggered treatment quality assurance can be performed. It is noted that operation 516 can be implemented in a wide variety of ways. For example, by acquiring the fluoroscopy during treatment at operation 516, the 4D (four-dimensional) imaging information can be matched to the 4D beam-time, lending itself to a 4D dose calculation. In various embodiments, this calculation can be summed in real-time at operation 516 for online quality assurance (QA) while the next beam is being delivered, allowing for 4D dose tracking for each fraction in the course of treatment. Note that operation 516 can be implemented in any manner similar to that described and/or shown by the present disclosure, but is not limited to such.

At operation 518, a computation can be made as to whether the treatment has been completed. If so, method 500 can proceed to operation 522. However, if it is computed at operation 518 that the treatment has not been completed, method 500 can proceed to operation 520. Note that operation 518 can be implemented in a wide variety of ways. For example, operation 518 can be implemented in any manner similar to that described and/or shown by the present disclosure, but is not limited to such.

At operation 520 of FIG. 5, move to the next beam position or angle. It is noted that operation 520 can be implemented in a wide variety of ways. For example, moving to the next beam position or angle at operation 520 can be implemented by rotating a gantry (e.g., 420). In various embodiments, moving to the next beam position at operation 520 can be implemented by rotating the patient. Note that operation 520 can be implemented in any manner similar to that described and/or shown by the present disclosure, but is not limited to such. After operation 520 is completed, method 500 can proceed to the beginning of operation 510.

At operation 522, an offline (or after treatment) triggered treatment quality assurance can be performed. Note that operation 522 can be implemented in a wide variety of ways. For example, by acquiring the fluoroscopy after treatment at operation 522, the 4D imaging information can be matched to the 4D beam-time, lending itself to a 4D dose calculation. In various embodiments, this calculation can be summed for offline quality assurance (QA) at operation 522 allowing for 4D dose tracking for each fraction in the course of treatment. In various embodiments, at operation 522 the offline triggered treatment quality assurance can include checking, making sure, and redelivering (or replaying) the dose computationally on the 4D image with the actual log files from the machine and verify the dose that was done. It is pointed out that this utilization of fluoroscopy for 4D dose tracking may be useful for standard radiation delivery schemes and dose-rates. It is noted that operation 522 can be implemented in any manner similar to that described and/or shown by the present disclosure, but is not limited to such. After the completion of operation 522, method 500 can be ended. In this manner, method 500 can perform triggered radiation therapy treatment in accordance with various embodiments of the present disclosure.

Figure 7:
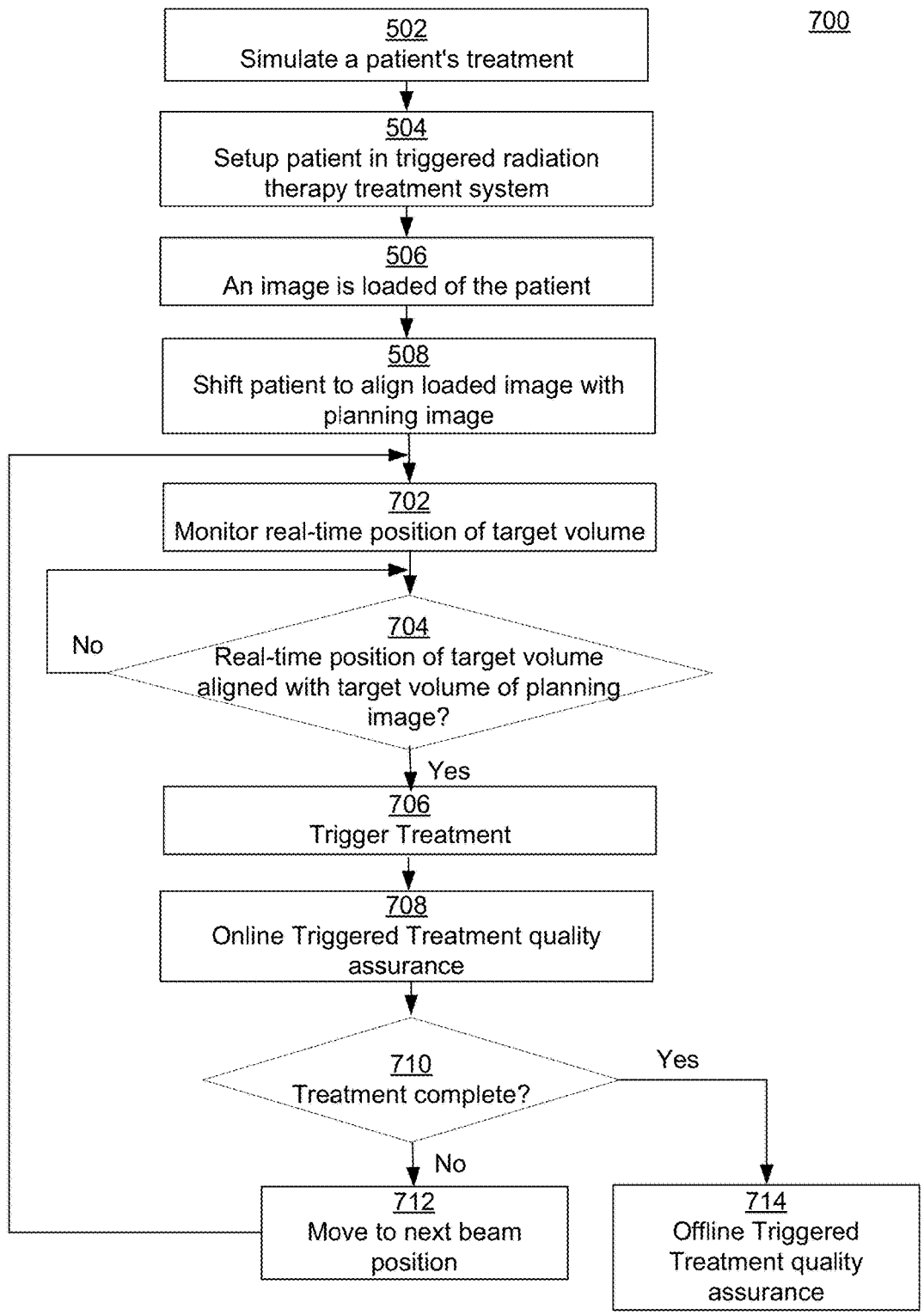
FIG. 7 is a flow diagram of a method in accordance with various embodiments of the present disclosure.

FIG. 7 is a flow diagram of a method 700 for performing triggered treatment (e.g., radiation therapy, ultrasound, etc.) in accordance with various embodiments of the present disclosure. Although specific operations are disclosed in FIG. 7, such operations are examples. The method 700 may not include all of the operations illustrated by FIG. 7. Also, method 700 may include various other operations and/or variations of the operations shown. Likewise, the sequence of the operations of flow diagram 700 can be modified. It is appreciated that not all of the operations in flow diagram 700 may be performed. In various embodiments, one or more of the operations of method 700 can be controlled or managed by software, by firmware, by hardware or by any combination thereof, but is not limited to such. Method 700 can include processes of various embodiments of the present disclosure which can be controlled or managed by a processor(s) and electrical components under the control of computer or computing device readable and executable instructions or code (e.g., the optimizer model 150 of FIG. 1). The computer or computing device readable and executable instructions (or code) may reside, for example, in data storage features such as computer or computing device usable volatile memory, computer or computing device usable non-volatile memory, and/or computer or computing device usable mass data storage. However, the computer or computing device readable and executable instructions (or code) may reside in any type of computer or computing device readable medium or memory (e.g., like those found within the computing system 100 of FIG. 1).

In various embodiments, note that the operations 502, 504, 506, and 508 of FIG. 7 can be performed similar to the operations 502, 504, 506, and 508 of FIG. 5 as described and/or shown by the present disclosure, but are not limited to such. It is noted that after the completion of operation 508 of FIG. 7, method 700 proceeds to operation 702 of FIG. 7.

At operation 702 of FIG. 7, treatment of the patient begins with monitoring (or continuously tracking) the real-time position of at least one target volume of the patient. Note that operation 702 can be implemented in a wide variety of ways. For example, monitoring (or continuously tracking) the real-time position of at least one target volume of the patient at operation 702 can be implemented with, but is not limited to, real-time fluoroscopic imaging, magnetic resonance imaging (MRI), fiducial markers, cone beam computed tomography (CBCT), digital tomosynthesis (DTS), ultrasound, external markers, any form of visualizing internal anatomy, surrogates of internal anatomy, 4D cone beam resulting in a real-time video feed, and the like. It is noted that operation 702 can be implemented in any manner similar to that described and/or shown by the present disclosure, but is not limited to such.

At operation 704, a computation can be made (e.g., manually or automatically) as to whether the real-time position of the at least one target volume substantially aligns with the position of the corresponding at least one target volume of the planning image. If so, method 700 can proceed to operation 706. However, if at operation 704 it is computed that the real-time position of the at least one target volume does not substantially align with the corresponding at least one target volume of the planning image, method 700 can proceed to the beginning of operation 704.

It is noted that operation 704 can be implemented in a wide variety of ways. For example, at operation 704, a manual monitoring can be implemented by a human (e.g., a therapist) that is trained to watch the real-time position of the at least one target volume and determine when it substantially aligns (e.g., within a range of deviation) with the corresponding at least one target volume from the planning image (e.g., CT, MRI, or other medical imaging). In various embodiments, at operation 704, an automatic monitoring can be included using a computing system (e.g., 100) wherein one or more metrics are defined in order to compute when the real-time position of the at least one target volume substantially aligns (e.g., within a range of deviation) with the corresponding at least one target volume from the planning image (e.g., CT, MRI, or other medical imaging).

In various embodiments, operation 704 of FIG. 7 can be implemented utilizing a visual representation of the mapping and alignment (e.g., within a range of deviation) of the real-time position of the at least one target volume and the corresponding at least one target volume from the planning image (e.g., CT, MRI, or other medical imaging) in any manner similar to that described and/or shown by the present disclosure, but is not limited to such. In various embodiments, it is noted that operation 704 of FIG. 7 can be implemented in any manner similar to operation 512 of FIG. 5 as described and/or shown by the present disclosure, but is not limited to such.

At operation 706, a treatment is triggered which can include, but is not limited to, delivering a dose of radiation therapy (or ultrasound, etc.) to the at least one target volume within a fraction of a second (e.g., less than a second). Note that operation 706 can be implemented in a wide variety of ways. For example, at operation 706, the entire treatment dosage of radiation therapy can be delivered to the at least one target volume within less than a second. In various embodiments, at operation 706, a fraction of the treatment dosage of radiation therapy can be delivered to the target volume within less than a second. In various embodiments, at operation 706, each beam can deliver a relatively high dose in a relatively short period of time. For example, each beam can deliver, but is not limited to, at least 0.01 Gy or 4 Gy in less than one second, and may deliver as much as 20 Gy or 500 Gy or more in less than one second (sec). In various embodiments, at operation 706, each beam can deliver, but is not limited to, greater than 4 Gy/sec, greater than 20 Gy/sec, or greater than 40 Gy/sec. In various embodiments, at operation 706, each beam can deliver, but is not limited to, at least 1 Gy in 0.25 sec, at least 1 Gy in 0.05 sec, or at least 1 Gy in 0.025 sec. It is noted that operation 706 can be implemented in any manner similar to that described and/or shown by the present disclosure, but is not limited to such.

At operation 708 of FIG. 7, an online (or during treatment) triggered treatment quality assurance can be performed. It is noted that operation 708 can be implemented in a wide variety of ways. For example, by acquiring the data (or information) of the real-time position monitoring of the at least one target volume during treatment at operation 708, it can be matched to the 4D beam-time, lending itself to a 4D dose calculation. In various embodiments, this calculation can be summed in real-time at operation 708 for online quality assurance (QA) while the next beam is being delivered, allowing for 4D dose tracking for each fraction in the course of treatment. Note that operation 708 can be implemented in any manner similar to that described and/or shown by the present disclosure, but is not limited to such.

At operation 710, a computation can be made as to whether the treatment has been completed. If so, method 700 can proceed to operation 714. However, if it is computed at operation 710 that the treatment has not been completed, method 700 can proceed to operation 712. Note that operation 710 can be implemented in a wide variety of ways. For example, operation 710 can be implemented in any manner similar to that described and/or shown by the present disclosure, but is not limited to such.

At operation 712 of FIG. 7, move to the next beam position or angle. It is noted that operation 712 can be implemented in a wide variety of ways. For example, moving to the next beam position or angle at operation 712 can be implemented by rotating a gantry (e.g., 420). In various embodiments, moving to the next beam position at operation 712 can be implemented by rotating the patient. Note that operation 712 can be implemented in any manner similar to that described and/or shown by the present disclosure, but is not limited to such. After operation 712 is completed, method 700 can proceed to the beginning of operation 702.

At operation 714, an offline (or after treatment) triggered treatment quality assurance can be performed. Note that operation 714 can be implemented in a wide variety of ways. For example, by acquiring the data (or information) of the real-time position monitoring of the at least one target volume after treatment at operation 714, it can be matched to the 4D beam-time, lending itself to a 4D dose calculation. In various embodiments, this calculation can be summed for offline quality assurance (QA) at operation 714 allowing for 4D dose tracking for each fraction in the course of treatment. In various embodiments, at operation 714 the offline triggered treatment quality assurance can include checking, making sure, and redelivering (or replaying) the dose computationally on a 4D image (for example) with the actual log files from the machine and verify the dose that was done. It is pointed out that in various embodiments, this utilization of fluoroscopy (or other position monitoring technique) for 4D dose tracking may be useful for standard radiation delivery schemes and dose-rates. It is noted that operation 714 can be implemented in any manner similar to that described and/or shown by the present disclosure, but is not limited to such. After the completion of operation 714, method 700 can be ended. In this manner, method 700 can perform triggered treatment (e.g., radiation therapy, ultrasound, etc.) in accordance with various embodiments of the present disclosure.

The foregoing descriptions of various specific embodiments in accordance with the present disclosure have been presented for purposes of illustration and description. They are not intended to be exhaustive or to limit the present disclosure to the precise forms disclosed, and many modifications and variations are possible in light of the above teaching. The present disclosure is to be construed according to the Claims and their equivalents.

What is claimed is:

1. A radiation therapy method comprising:
loading a planning image of a target in a human;
monitoring the position of said target;
computing an occurrence of substantial alignment between the position of said target and said target of said planning image, said computing comprises utilizing a sum of a real-time deformation vector-field; and
after said computing, triggering a beam of radiation to deliver a dosage to said target in less than a second.

2. The method of claim 1, wherein said planning image comprises a magnetic resonance imaging (MRI) image.

3. The method of claim 1, wherein said monitoring comprises performing fluoroscopy.

4. The method of claim 1, wherein said planning image comprises a computed tomography (CT) image.

5. The method of claim 1, wherein said triggering is performed manually by a human.

6. The method of claim 1, wherein said computing comprises a visual representation of said sum of said real-time deformation vector-field.

7. The method of claim 1, wherein said monitoring comprises generating a real-time image of said target.

8. The method of claim 1, wherein said computing comprises a visual representation comprising a bar graph.

9. A radiation therapy method comprising:
loading a planning image of a target in a human;
monitoring the position of said target;
mapping said target in both said monitoring and said planning image;
computing an occurrence of substantial alignment between the position of said target and said target of said planning image, said computing comprises utilizing a sum of a real-time deformation vector-field; and
after said computing, triggering a beam of radiation to deliver a fraction of a dosage to said target in less than a second.

10. The method of claim 9, wherein said planning image comprises a magnetic resonance imaging (MRI) image.

11. The method of claim 9, wherein said monitoring comprises performing fluoroscopy.

12. The method of claim 9, wherein said planning image comprises a computed tomography (CT) image.

13. The method of claim 9, wherein said triggering is performed manually by a human.

14. The method of claim 9, wherein said computing comprises a visual representation of said sum of said real-time deformation vector-field.

15. The method of claim 9, wherein said computing comprises a visual representation comprising a bar graph.

16. A radiation therapy method comprising:
loading a planning image of a target in a human;
monitoring the position of said target;
computing an occurrence of substantial alignment between the position of said target and said target of said planning image, said computing comprises utilizing a sum of a real-time deformation vector-field;

after said computing, triggering a beam of radiation to deliver a dosage to said target in less than a second; and after said triggering, performing quality assurance utilizing information associated with said monitoring.

17. The method of claim 16, wherein said planning image comprises a magnetic resonance imaging (MRI) image.

18. The method of claim 16, wherein said monitoring comprises performing fluoroscopy.

19. The method of claim 16, wherein said triggering is performed manually by a human.

20. The method of claim 16, wherein said computing comprises a visual representation comprising a bar graph.

\* \* \* \* \*